Figure 1:
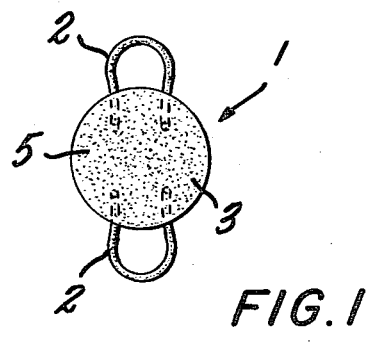

United States Patent [19]

Galin

[11] 4,240,163
[45] Dec. 23, 1980

[54] MEDICAMENT COATED INTRAOCULAR LENS

[76] Inventor: Miles A. Galin, 115 E. 38th St., New York, N.Y. 10016

[21] Appl. No.: 7,890

[22] Filed: Jan. 31, 1979

[51] Int. Cl.³ .......................... A61F 1/16; A61F 1/24
[52] U.S. Cl. .............................................. 3/13; 427/2
[58] Field of Search ............................ 3/13, 1; 427/2

[56] References Cited

U.S. PATENT DOCUMENTS

| | | | |
|---|---|---|---|
| 3,511,684 | 5/1970 | Huffaker | 3/1 X |
| 3,766,167 | 10/1973 | Lasker et al. | 424/180 X |
| 4,100,309 | 7/1978 | Micklus et al. | 427/2 |
| 4,170,043 | 10/1979 | Knight et al. | 3/13 |

OTHER PUBLICATIONS

"Corneal Endothelium Damage with Intraocular Lenses: Contact Adhesion Between Surgical Materials and Tissue" by Herbert E. Kaufman et al., Reprint from Science, Nov. 4, 1977, vol. 198, pp. 525-527 (4 pp.).
"Prevention of Endothelial Damage from Intraocular Lens Insertion" by Jeffrey Katz et al., *Tr. Am Acad. Ophth & Otol.*, vol. 83, Mar.-Apr. 1977, pp. 204-212.

*Primary Examiner*—Ronald L. Frinks
*Attorney, Agent, or Firm*—Brumbaugh, Graves, Donohue & Raymond

[57] ABSTRACT

An intraocular lens is coated with a compatible medicament, such as an anticoagulant, an anti-inflammatory agent or an anti-complement agent.

12 Claims, 2 Drawing Figures

U.S. Patent  Dec. 23, 1980  4,240,163

MEDICAMENT COATED INTRAOCULAR LENS

The present invention relates to an opthalmic prosthetic device, and more particularly to an anti-reactive coated intraocular lens, as well as medications which prevent reaction of an intraocular lens.

As is well known in the field of ophthalmology, an intraocular lens, when surgically implanted, is designed to replace a previously or simultaneously removed cataractous lens. The optical portion of such lenses may be of chemically pure polymethylmethacrylate or glass or any combination thereof. These are presumably biologically neutral materials. The optical portion may have supports of the same nature, or may be supported by loops made of nylon, polypropylene or metal. Nylon 66, i.e., polyhexamethylene adipamide, has been in eyes for nearly twenty years. Polypropylene is a more recent support system. An intraocular lens is small, having an overall diameter of approximately 13 mm, if it is a single piece of plastic or glass, or having an optical diameter of 5 to 6 mm and a tip-to-tip loop diameter of approximately 7 to 9 mm. The center thickness and posterior radii of the optical portion vary according to the power desired and the material utilized. An intraocular lens may weigh up to 20 mg in air, or 1 to 4 mg in aqueous medium. Intraocular lenses are commercially available from a variety of companies throughout the world.

Although the implantation of intraocular lenses has constituted an appreciable surgical advance, their use can still be improved upon significantly. For example, implantation of an intraocular lens may cause immediate or late damage to the corneal endothelium, immediate or late inflammatory responses in the anterior segment of the eye, immediate or late inflammatory responses in the posterior segment of the eye, and immediate or late secondary fibrosis and/or neovascularization. All in all, flare, cells, vitreous reaction, cystoid macular edema, hyopyon, uveitis and secondary glaucoma, are not rare occurrences immediately or shortly after implantation and have become an ever-increasing problem.

Accordingly, it is the principal object of the present invention to provide an improved intraocular lens and medications for the eye after lens implantation, which will overcome the above-mentioned problems in the use of an intraocular lens.

Figure 2:
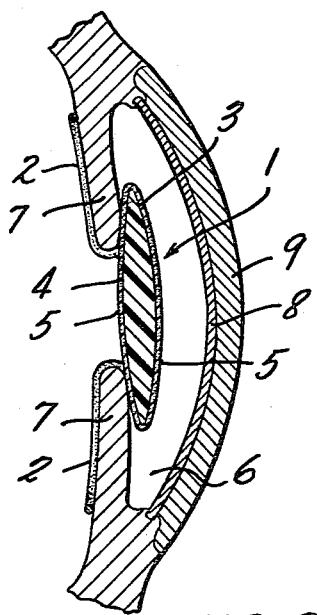

In the Drawing:

FIG. 1 is a nonscalar front or anterior view of a representative coated intraocular lens of the invention, and FIG. 2 is a nonscalar cross-sectional view of a representative coated intraocular lens of the invention as implanted within an eye.

When an intraocular lens is inserted, the mechanics of insertion may lead to adhesion of the lens to delicate intraocular structures where damage to these structures immediately ensues. Coating such a lens with a material which would fill in the microscopic crevices that are present, no matter how well the lens is polished, will reduce the trauma of such an event. Second, if this coating has an effect on platelets, fibrin and inflammatory materials, the lens may act as a therapeutic agent to prevent secondary reactions listed above.

It is the intent of the present invention to coat lenses with such a material and to provide medications as well which eliminate the lens stimulus to all of the untoward events characterized above. Generally, the coating will constitute from 1/10,000% to 1/10% by weight of the intraocular lens. The coating generally will have a thickness of 1/10,000 mm to about 1/100 mm.

Medicaments, which are compatible with the intraocular lens material, can be used to coat the lens. Suitable anticoagulant or anti-inflammatory medicaments include sulfated polysaccharides, such as sulfated hyaluronic acid, xylan sulfate, chitosan sulfate, chondroitin sulfate, dextran sulfate, heparin and, preferably, low-molecular weight heparin. In addition, since low-molecular weight heparin reduces platelet agglutination and is known to inhibit complement activity, white cell agglutination would be reduced and the enzymatic lysosomal released ingredients of white cells would have less opportunity to degrade the delicate intraocular content. Consequently, but not limited to, low molecular weight heparin can be used to reduce the white cell responses inside the eye. Other agents, of course, can be used that do the same.

Blockers of the standard complement system and the indirect complement system, which activate certain white cell reactions, can be utilized to coat the lens and/or be placed inside the eye and/or be placed on the cornea as therapy to prevent the complications listed above. Such anti-complement agents, but not limited to ethacrylic acid and prostaglandin inhibitors and certain steroids, can be used in this regard.

Commercially available heparin which usually has a molecular weight of from about 12,000 to about 15,000 daltons may lead to platelet agglutination. Consequently, low molecular weight heparin (a derivative or fraction) would be more suitable in the range of molecular weight of from about 2,500 to about 5,300 daltons and even somewhat higher. These low molecular weight heparins can be prepared by enzymatic hydrolysis or depolymerization of heparin with heparinase as disclosed in U.S. Pat. No. 3,766,167, or by depolymerizing either heparin residues or commercial porcine or bovine heparin by reacting the heparin material with a blend of ascorbic acid and hydrogen peroxide, the reaction products then being isolated and fractionated by precipitation using an organic solvent, such as ethanol, methanol, acetone, methyl ethyl ketone or dioxime.

The medicament coated intraocular lens can be prepared by any appropriate well known coating technique, such as immersion coating, spray coating and the like, using a suitable solution or dispersion of the medicament dissolved or dispersed in an appropriate solvent or dispersant, such as water, ethanol, acetone, and the like. The coating solution or dispersion has a conventional concentration of medicament which corresponds to the particular coating technique selected. After the coating is applied to the intraocular lens, it is dried, for example, by drying at room temperature or above. The coating can be repeatedly applied, if necessary, to achieve the desired coating weight or thickness.

The same coating can be used as a topical or subconjunctival medication. It has been found that the anticoagulant, anti-white blood cells, anti-complement, anti-inflammatory medicament coated intraocular lens of the present invention upon implantation can reduce damage to the corneal endothelium upon contact and upon the secondary responses of inflammatory cellular response. Both these preventatives reduce the potential for adhesions, synechias, inflammation, cystoid macular edema, vitritis, cyclitis, uveitis and all secondary effects of inflammation. The anticoagulant, anti-inflammatory groups of medicament coated intraocular lenses, for example, were found to inhibit blood clotting from occurring, as well as white blood cell clotting (hyopyon) on the lens proper and reduce inflammation in general. The prevention of white blood cell clotting on the lens leading to keratic precipitates improves patient vision, reduces the need for other medication and allows a more rapid recuperation.

Even though the intraocular lens is coated, the coating was not found to effect adversely spectral transmission in the visible range of the optical portion of the intraocular lens. It was further found that any elution, for example, of the materials on the lens was beneficial and in no way obstructed the efficacy of the lens.

Referring to FIGS. 1 and 2 of the drawing, the representative coated intraocular lens 1 of the invention has two or more supporting loops 2. The anterior or front surface 3 of the intraocular lens 1 (and also the posterior or rear surface 4, if desired, of the intraocular lens 1) has a medicament coating 5 thereon.

As shown in FIG. 2, the intraocular lens 1 is implanted within the anterior chamber 6 of the eye containing aqueous humor and held in place by engagement of the loops 2 with the iris 7. The intraocular lens 1 is behind the corneal endothelium layer 8 of the cornea 9.

What is claimed is:

1. An intraocular lens coated with a compatible medicament, said medicament being selected from the group consisting of a sulfated polysaccharide and ethacrylic acid.

2. The intraocular lens defined by claim 1 wherein the medicament is a sulfated polysaccharide.

3. The intraocular lens defined by claim 2 wherein the sulfated polysaccharide is heparin having a molecular weight of from about 12,000 to about 15,000 daltons.

4. The intraocular lens defined by claim 2 wherein the sulfated polysaccharide is low molecular weight heparin having a molecular weight of from about 2,500 to about 5,300 daltons.

5. The intraocular lens defined by claim 2 wherein the sulfated polysaccharide is dextran sulfate.

6. The intraocular lens defined by claim 2 wherein the sulfated polysaccharide is chondroitin sulfate.

7. The intraocular lens defined by claim 2 wherein the sulfated polysaccharide is chitosan sulfate.

8. The intraocular lens defined by claim 2 wherein the sulfated polysaccharide is xylan sulfate.

9. The intraocular lens defined by claim 2 wherein the sulfated polysaccharide is sulfated hyaluronic acid.

10. The intraocular lens defined by claim 1 wherein the medicament is ethacrylic acid.

11. The intraocular lens defined by claim 1 wherein the coating constitutes from about 1/10,000% to about 1/10% by weight of the intraocular lens.

12. The intraocular lens defined by claim 1 wherein the coating has a thickness of from about 1/10,000 mm to about 1/100 mm.

* * * * *